(12) United States Patent
Chervitz et al.

(10) Patent No.: US 6,283,996 B1
(45) Date of Patent: Sep. 4, 2001

(54) ADJUSTABLE LENGTH STRAP AND FOOTING FOR LIGAMENT MOUNTING AND METHOD FOR ITS USE

(75) Inventors: Alan Chervitz; E. Marlowe Goble, both of Logan; Thomas Wade Fallin, Hyde Park, all of UT (US)

(73) Assignee: Medicine, Lodge, Inc., Logan, UT (US)

( * ) Notice: Subject to any disclaimer, the term of this patent is extended or adjusted under 35 U.S.C. 154(b) by 0 days.

(21) Appl. No.: 09/024,156

(22) Filed: Feb. 17, 1998

Related U.S. Application Data

(62) Division of application No. 08/717,094, filed on Sep. 20, 1996, now abandoned.

(51) Int. Cl.[7] .................................................. A61F 2/08
(52) U.S. Cl. ........................................................ 623/13.14
(58) Field of Search ............................. 623/13.11, 13.12, 623/13.13, 13.14, FOR 13; 606/72

(56) References Cited

U.S. PATENT DOCUMENTS

| | | | |
|---|---|---|---|
| 4,772,286 | * | 9/1988 | Goble et al. ............................ 623/13 |
| 4,828,562 | * | 5/1989 | Kenna ..................................... 623/13 |
| 5,456,721 | * | 10/1995 | Legrand .................................. 623/13 |

* cited by examiner

Primary Examiner—David H. Willse
(74) Attorney, Agent, or Firm—M. Reid Russell

(57) ABSTRACT

A ligament mounting and method for its use for endosteally mounting an end of a ligament graft in a prepared bone tunnel section in a surgical procedure to replace a patient's ligament. The ligament mounting includes a strap and footing combination that are suitable for human implanting and may be formed from a material that is absorbed by the patient's body during the healing process. The strap is formed as a section of flexible material, includes a proximal end for passage through a footing that is for arrangement across a cortex end of the ligament tunnel section, and with the strap distal end arranged to connect to a ligament graft end. The strap and footing are formed to allow for passage of the strap in one direction and to bind when the footing is compressed to crimp onto said strap, prohibiting it from being pulled back through the footing when a pulling force is applied, maintaining a ligament graft under tension in the tunnel section endosteum.

8 Claims, 6 Drawing Sheets

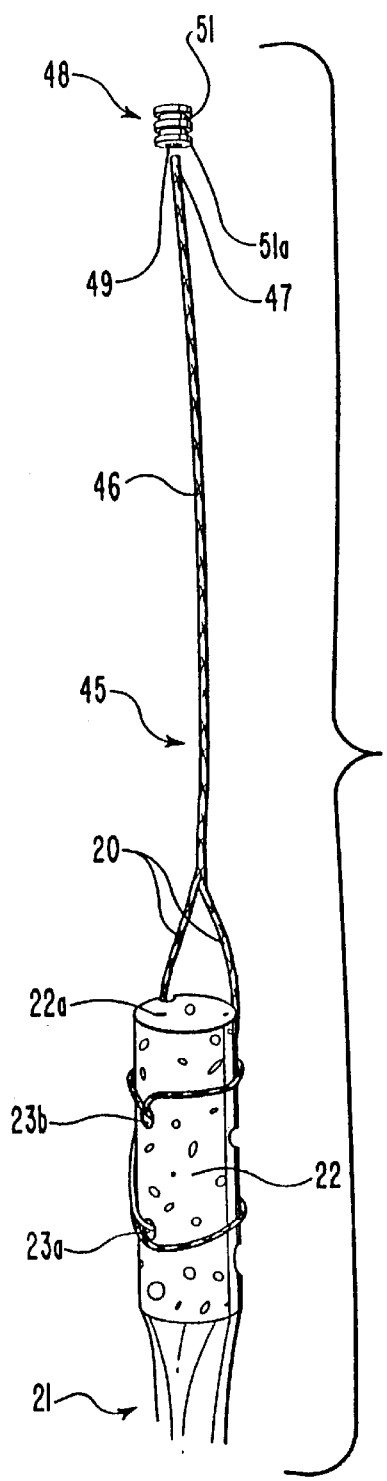
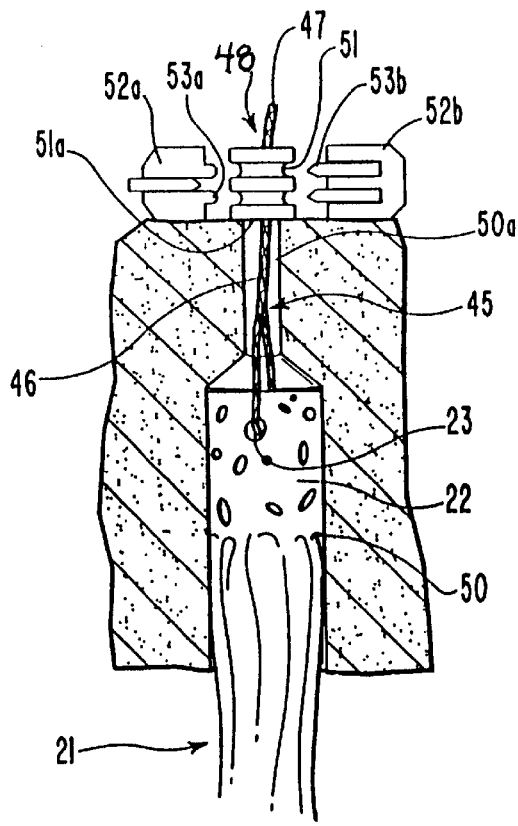
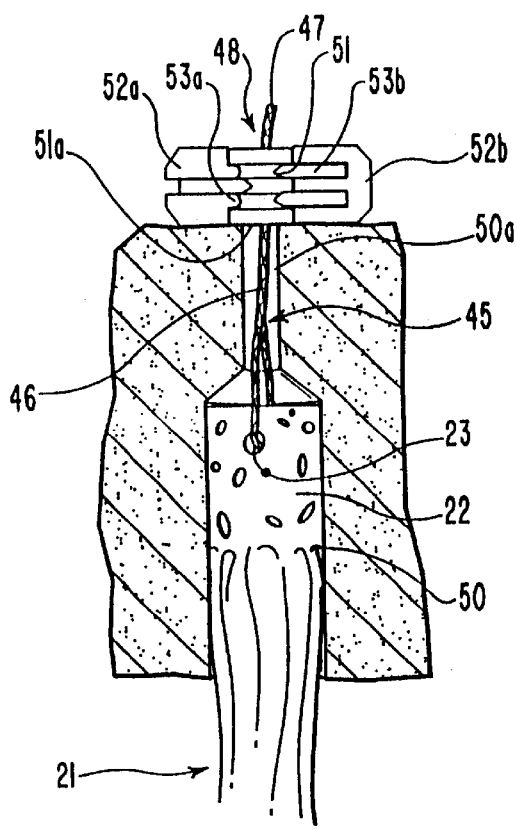
FIG. 7
FIG. 8A
FIG. 8B

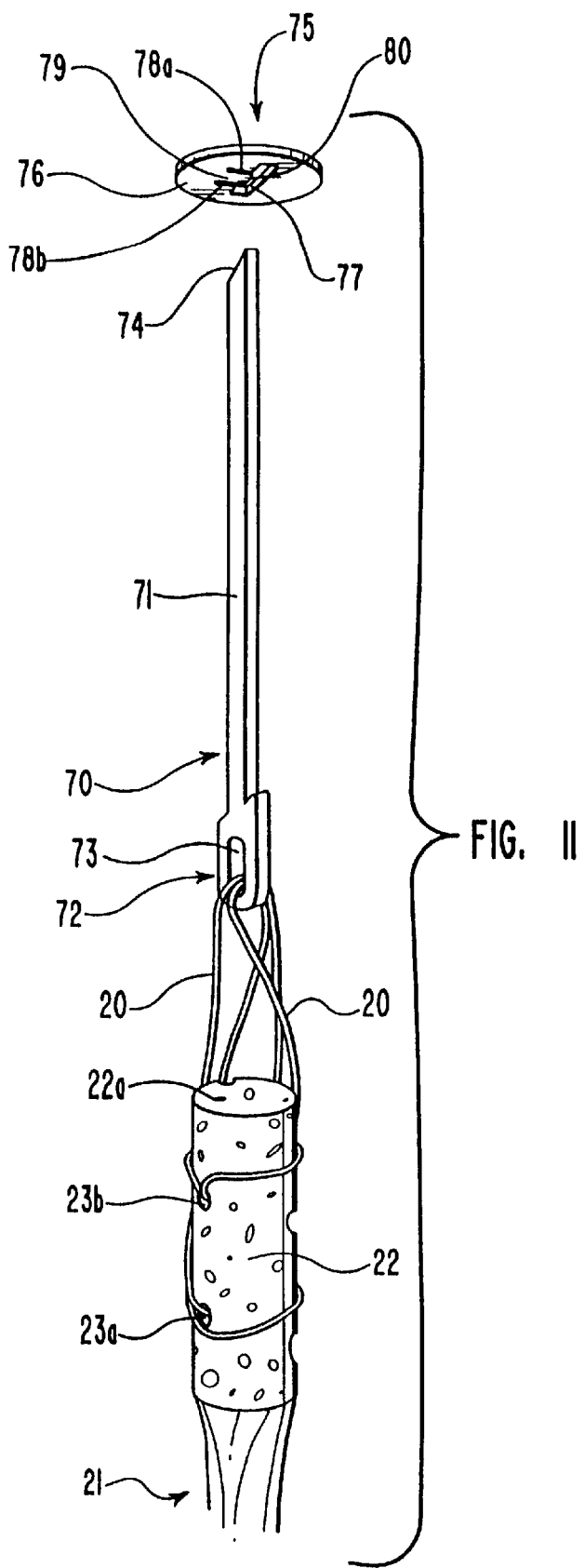

ADJUSTABLE LENGTH STRAP AND FOOTING FOR LIGAMENT MOUNTING AND METHOD FOR ITS USE

This is a division of application Ser. No. 08/717,094, filed Sep. 20, 1996, now abandoned.

BACKGROUND OF THE INVENTION

1. Field of the Invention

This invention relates to devices and methods for use in a ligament repair or replacement surgical procedure for fitting and mounting a ligament graft end in a prepared ligament tunnel.

2. Prior Art

In a practice of an arthroscopic surgical procedure for repair or replacement on an anterior or posterior cruciate ligament, that the invention is suitable for use in, a pair of tunnel sections are drilled into the distal femur and proximal tibia, respectively, to intersect the ligament points of origin.

In which procedure a system is provided for fitting a ligament graft in the tunnel sections, securing one end therein and applying a desired tension to the other ligament end and securing it. A number of systems have been developed to provide for fitting a ligament graft end into which tunnel sections, including a mounting of a ligament graft end to a device for pulling it through a tunnel section end. One such device is a suture sling that is suitable for such use and can be arranged for use with the present invention.

Such a suture sling can be utilized with the present invention that is mounted to a bone end of a bone tendon bone graft. The suture sling is used for pulling a graft bone end through aligned tunnel sections with the ligament mounting of the present invention secured to the suture sling and for mounting in the ligament tunnel or at a tunnel end.

Additionally, one or both of the inventors have heretofore developed a number of cruciate ligament mounting arrangements and methods such as, for example, U.S. Pat. Nos. 4,772,286; 4,870,957; 4,927,421; 4,997,433; 5,129,902; 5,147,362 and Re. 34,293, and other persons have also developed ligament graft mountings, for example U.S. Pat. Nos. 4,301,551; 4,605,414; 4,744,793; 4,950,270 and 5,139,520. None of which earlier devices, arrangements and methods, however, have involved a device secured to a ligament end to slide through a footing to lock thereto that, for the invention, includes a combination of the straight flexible strap and footing and includes locking members for locking the strap in the footing, which strap, in turn, connects to a suture sling or other ligament attachment arrangement, nor have such earlier devices and arrangements taught a method like that of the invention.

While graft attachment and anchoring devices have been heretofore utilized, and such an arrangement for anchoring a ligament graft in a ligament replacement procedure is shown in U.S. Pat. No. 5,306,301 such provides a footing only and teaches a complicated draw string arrangement that is different to use and secure and is unlike the strap and footing of the invention and its use. Also while strap and footings have been heretofore used, and examples of such arrangements and their uses are shown in U.S. Pat. Nos. 5,306,301; 5,500,000; and 5,520,691, such have been as mounting for securing an item, such as a ligament suture, or the like onto a bone surface, none have utilized a sliding strap and footing with a locking arrangement combination, along with a ligament end tether such as a suture sling arrangement, or the like, to easily adjust tension on and mount a bone tendon bone type ligament graft, or the like, in a tunnel section proximate to or at a tunnel segment cortex end, that is like that of the present invention.

SUMMARY OF THE INVENTION

It is a principal object of the present invention to provide embodiments of an adjustable length strap and footing with locking arrangement for use for mounting a ligament end, where the strap distal end is for connecting to a ligament graft end as by a suture or suture sling or directly thereto, and enables a pulling of the ligament graft end along a tunnel section or sections, with the proximal strap end to fit through a footing positioned across the tunnel section cortex end and provides for locking the strap to the footing at a selected point along that strap where a proper tension is applied to the ligament end as a ligament end mounting.

Another object of the present invention is to provide an adjustable length strap and footing for ligament mounting where the strap is arranged to slide through a hole formed through the footing shortening the distance between the strap distal end and footing, with the footing arranged to lock onto the strap thereat, providing a desired strap length relative to the footing.

Another object of the present invention is to provide an adjustable length strap and footing for ligament mounting where the strap is arranged to receive, preferably secured to its distal end, a ligament graft end or a suture or suture sling arrangement that, in turn, connects to a ligament graft end.

Still another object of the present invention is to provide an adjustable length strap and footing for ligament mounting where the strap is formed as a single unit, preferably from a flexible material, such as a plastic, to include locking members formed at spaced intervals therealong, that is formed as a disk with a center hole therethrough which footing hole is formed to slightly compress each locking member as it passes therethrough, and flexes outwardly to where the locking member edge extends over the hole edge locking thereto when a force is applied to pull the strap distal end back through the footing hole.

Still another object of the present invention is in another embodiment of an adjustable length strap arranged as a thread, chain, cable, or the like, or even a suture, to fit through a footing that can be crimped onto the strap at a selected position therealong.

Still another object of the present invention is to provide still another embodiment where the adjustable length strap can be smooth walled or have greater and lesser diameter segments formed therealong for fitting through a footing center hole that is formed to include a locking panel or cantilever elements to be elevated by passage of the strap through the footing in one direction and lock to the strap when pulled oppositely as when the connected ligament graft is placed under tension.

Still another object of the present invention is to provide an adjustable length strap and footing for ligament mounting of a ligament graft end, under tension, in a prepared ligament tunnel, that is easy, convenient and reliable to use in a ligament repair procedure and, as appropriate, can be formed of a material to be absorbed by a patient's body during a healing process.

The present invention is in an adjustable length strap and footing for use in mounting a ligament graft end in a prepared ligament tunnel formed into a bone. For mounting the femoral end of a ligament graft utilizing the invention, the femoral tunnel is initially drilled as a first tunnel section to within the bone endosteum, with further drilling then taking place to extend the tunnel as a second tunnel section, that passes through the posterior cortex utilizing a same or lesser diameter drill than used to drill the first tunnel section. The invention provides a straight strap for mounting directly or through sutures to a ligament graft end on its distal end. The strap body includes, locking members, formed therealong that can be a series of right angle teeth that slope towards the strap distal end, a number of spaced cone members that slope towards the strap distal end, a chain having greater diameter and adjacent lesser diameter components, or a straight bar can be employed that is for fitting into a footing that includes a locking panel. Further, a thread, cord, chain, or even a suture section the strap for fitting through a footing that can be squeezed or crimped thereon, or the like. The strap is preferably pointed at its proximal end and that is to fit through the footing, that for the series of teeth, spaced cones, or the like, is preferably a washer or disk having a center transverse hole that is slightly smaller in diameter than the strap cross section at a tooth apex or a cone skirt. Whereby the individual spaced teeth or cones will travel therethrough, traveling past an edge or lip of which center transverse hole, to lock against that edge or lip when the strap is pulled back through the hole as when a tension is applied to the strap distal end, providing a ligament end mounting.

The strap may be formed as a straight section from a flexible material, such as a plastic, fabric, chain, material, or the like, and includes, as a distal end, a transverse eyelet, and is preferably pointed at its proximal end. The transverse eyelet end can receive a ligament graft, or the like, looped therethrough or can receive a suture, sutures, or a suture sling, that is preferably an arrangement of at least a pair of sutures, or can be connected directly to a ligament graft end. Such ligament graft, for example, can be a bone tendon bone ligament graft.

The strap, with a ligament graft secured to its distal end, is moved through a prepared ligament tunnel section to where the strap proximal pointed end extends through a cortex end of the tunnel section. Thereat, the footing, that has a center hole formed therethrough, is fitted onto the strap proximal end. In which fitting, the strap pointed end will have passed through the footing center hole, and the strap, is then pulled therethrough. The footing center hole is formed to have a diameter or shape such that its edge will resist passage of the strap therethrough, causing a locking member component of the strap or footing, to be some what compressed. The locking member that is a skirt, edge, tooth apex, or the like, on the strap or a locking pawl, cantilever, elements, or the like formed in the footing hole, will flex to lock the footing and shaft together when a force is applied to the strap to pull it back through the hole. Travel of the strap through the disk hole thereby continues until a tension is applied to the strap to pull it back through the disk hole whereat the locking member locks the strap and footing together. When such force is applied to the strap, in the embodiments where the strap has locking members formed therealong, the edge of the locking member that has just passed through the disk hole extends across the disk hole edge and prevents strap passage back through the disk hole. Alternatively, the locking member can be a straight thin bar, cord, chain or strand, the passes across a footing locking pawl, or cantilever elements formed adjacent to the footing hole, the pawl or cantilever elements engaging the bar, cord, chain, or strand surface when it is pulled back. A tension can be applied through strap as by placing the ligament graft opposite end in tension. Thereafter, should an increase in the tensile stress applied to the ligament graft be required, the strap can be further pulled through the footing, the locking member releasing and then connecting to the strap to prohibit strap withdrawal, or, where the strap is a cord, thread, chain, or the like, the footing can be arranged as a cylinder to be crimped onto to lock to a selected site or location along that strap when the connected ligament is under a selected tension.

The strap that includes a locking member or members is preferably formed from a strong but flexible material, preferably a plastic, and that plastic can be selected to be biodegradable so as to be absorbed by the body during healing. The locking members that are arranged along the strap are preferably integral thereto and may, as with a use of a series of cones connected apex to base, or the like, as the strap, can be used to form the strap, or the locking members, such as right angle teeth, can be formed along a shaft side during formation of the strap, or the like. Preferably, the narrow bar strap is also formed of a plastic where the locking pawl can bite therein and may be biodegradable, and the cord, thread, or chain can also be formed to be biodegradable. For each locking member arrangement the footing is provided with a transverse hole that is formed to pass the strap upwardly therethrough, and includes an edge or edges, locking pawl, cantilever elements, or the like, to prohibit the strap from being pulled back out of the footing. The embodiments of the strap, locking members and footings of the invention are all to provide a ligament mounting to an end of a ligament graft that is placed under tension.

DESCRIPTION OF THE DRAWINGS

In the drawings that illustrate that which is present regarded as the best modes for carrying out the invention:

FIG. 7 is a profile perspective view, like that of FIGS. 1 and 2, of a third embodiment of an adjustable length strap and a footing for crimping thereto of the invention showing a braided pair of sutures, that attach, as a cradle, to a ligament end, with the braided distal end aligned for fitting through a cylindrical footing;

FIG. 8A is a side elevation view of a section of bone wherein a first tunnel section is shown as having been drilled, with a lesser diameter second tunnel section shown extending from the first tunnel section end, and passing through the bone cortex and showing the strap of FIG. 7 fitted through the first tunnel section, with the strap end fitted through the crimping footing to where the ligament end is pulled fully into the first tunnel section;

FIG. 8B is a view like FIG. 8 only showing the footing sides as having been squeezed together crimping it onto to so as to lock it onto the strap;

FIG. 11 is a profile perspective view like that of FIGS. 1, 2, 7 and 10, showing a fifth embodiment of an adjustable length strap and footing with the strap shown as a flat bar with an eyelet distal end wherethrough sutures are of a suture sling are fitted with the bar proximal end shown aligned for fitting through a footing that includes a locking pawl formed adjacent to its transverse hole.

DETAILED DESCRIPTION

Figure 1:
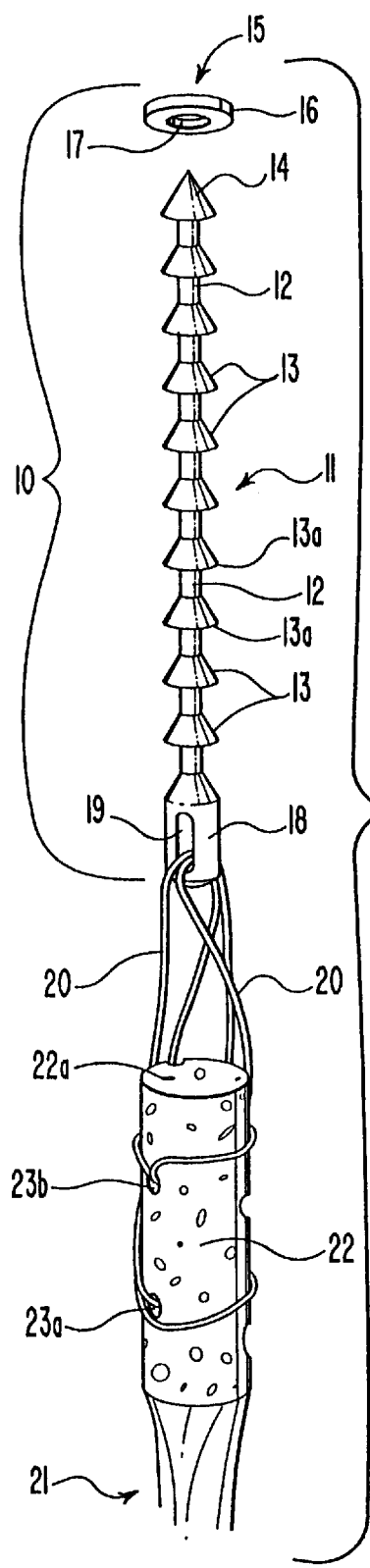
FIG. 1 is a profile perspective view of a first embodiment of an adjustable length strap and footing of the invention, showing a strap distal end thereof connected to a suture sling arrangement that is, in turn, secured to a bone end of a bone tendon bone ligament graft, with the strap shown formed from a number of frustum cones that are connected end to end as locking members, and with a strap proximal end shown as pointed and aligned for passage through a footing that is shown as a disk with a center hole formed therethrough.

FIG. 1 shows a first embodiment of an adjustable length strap and footing for a mounting 10 of the invention for mounting a ligament end in a bone tunnel, hereinafter identified as ligament mounting 10. The ligament mounting 10 is shown in this embodiment to include a strap 11, that is preferably formed as a single unit, and is shown in FIG. 1 as a series or chain of cone shaped locking members 13, that are each frustum cones, and extend at equal spaced intervals outwardly from along a center rod body 12. A top or distal strap end is shown as having a pointed cone 14 formed thereacross that is aligned for fitting through a footing 15. Footing 15 is here shown as flat disk 16 that has a center hole 17 formed therethrough. The strap distal end is here shown as a cylinder 18 as an axial extension of the body 12 that includes a slot 19 formed therethrough to function as an eyelet and receives a pair of sutures 20 threaded therethrough. The sutures 20 are here shown configured as a sling.

The sutures 20 are configured as a sling from a pair of sutures that are each connected to be continuous, but, of course can be a single suture only, and an end of which sling is passed through the eyelet slot 19. In practice, the pair of continuous sutures are each formed into a fold for fitting, respectively, through lower and upper transverse holes 23a and 23b, that are formed through a bone end 22 of a bone tendon bone ligament graft 21. These transverse holes 23a and 23b are preferably parallel, are spaced apart and are drilled so as to align with one another. A preferred method for mounting the sutures 20, as a sling, to the bone end 22, involves fitting a first suture 20, at a fold therein, through one end of the lower transverse hole 23a. Whereafter, the first suture 20 fold is opened, forming loop that is then passed over a top surface 22a of the bone end 22 and is slid down along the bone end surface. So arranged, the fold will be approximately positioned over the lower transverse hole 23a end that the first suture was fitted into. The first suture 20 is then pulled back through the transverse hole 23a, tightening the loop around the bone end 22 surface. Thereafter, a loop is formed in the other or second suture 20 that is then fitted through the upper transverse hole 23b. The suture 20 fold travels through the transverse hole 23b end that is opposite to the end of the lower transverse hole 23a that the first suture 20 fold was fitted into. Thereafter, the second suture 20 fold is opened into a loop that is fitted over the bone end face 22a. The second suture 20 is then pulled back through the upper hole 23b, tightening it around the bone end, as shown in FIG. 1. So arranged, the sutures 20 extend along the bone end 22 and are spaced apart from one another.

When the suture 20 sling is pulled axially through a ligament tunnel section the bone end 22 will essentially follow it along that ligament tunnel section. The same suture sling method of formation is appropriate for mounting to all the bone ends of the bone tendon bone ligament grafts shown in FIGS. 1, 2 and 7, and a single suture utilized as a suture sling is shown mounted to a bone end in FIGS. 3, 4, 6, 9 and 10A. It should therefore be understood that any sling arrangement for mounting to a ligament end is suitable for use with the embodiments of the invention as set out and described herein, within the scope of this disclosure.

Figure 3:
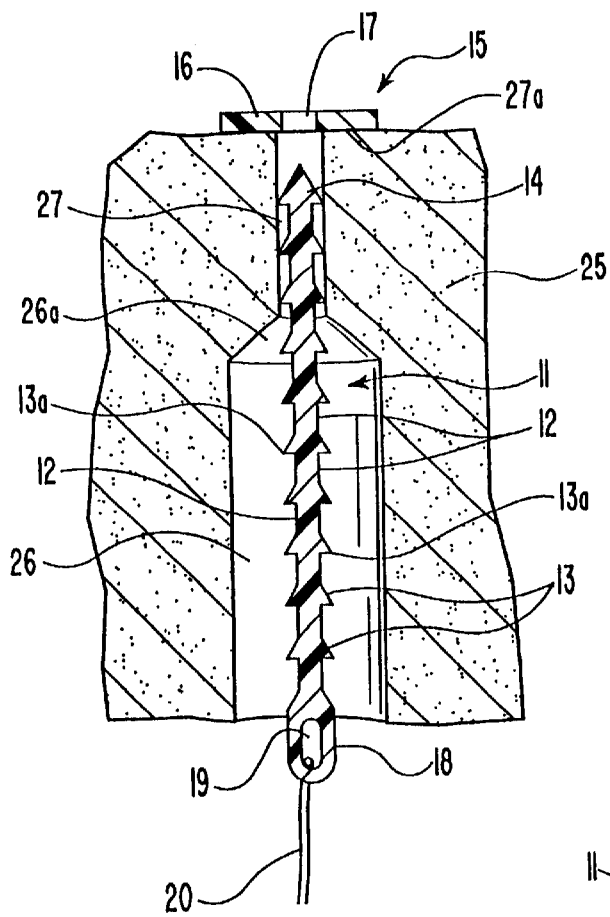
FIG. 3 is a side elevation view of a section of bone wherein a first tunnel section is shown as having been drilled with a lesser diameter second tunnel section shown extending from the first tunnel section end and passing through the bone cortex, and showing the adjustable length strap of FIG. 1, whereto a ligament graft is connected by sutures that have been fitted through the first tunnel section and into the second tunnel section with a footing positioned across the second tunnel section cortex end.
Figure 4:
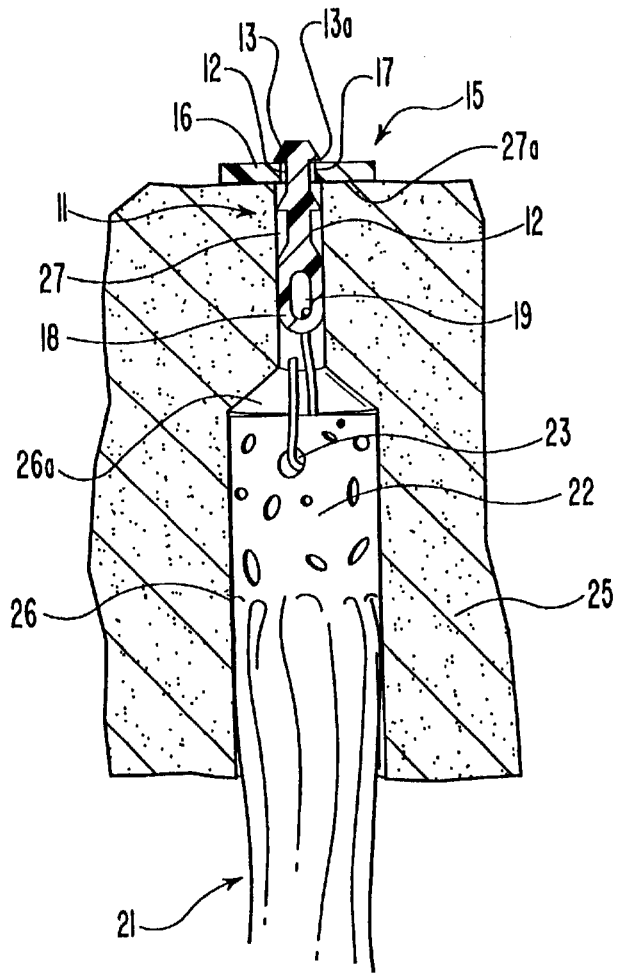
FIG. 4 is a view like that of FIG. 3 only showing the strap as having been pulled through the footing, and with the strap shown as having been cut off above a locking member and showing a bone end of the ligament graft connected to the strap by a pair of sutures.

FIGS. 3 and 4 show the ligament mounting 10 as including the single suture 20 loop fitted through the strap 11 eyelet slot 19. In FIG. 4, the suture 20 loop is shown passed through hole 23 formed in a bone end 22 of bone tendon bone graft 21. Shown in FIG. 3, with the ligament graft mounted by suture 20 to the strap 11, the strap is passed into a first straight tunnel section 26 that has been formed in a bone section 25 that is a section of a patient's bone, such as their distal femur. In such procedure the ligament graft 21 is used as a replacement for a patient's damaged ligament. Though, it should be understood the embodiments of the strap and footing of the invention, as shown and described herein, can be used for a number of procedures that involve securing a ligament graft end in a patient's bone.

The first tunnel section 26, as shown in FIGS. 3 and 4, terminates in tunnel end 26a in the bone section 25 endosteum. A second straight tunnel section 27 is then drilled through the first tunnel section end 26a, axially to that first tunnel section, to exit the bone cortex at 27a. In FIG. 3, the footing 15, shown herein as a disk 16, is positioned across the second tunnel section end 27a such that the center hole 17 formed therethrough is in alignment with the second tunnel section cortex end and the pointed end of a top cone 14 of the series of frustum cones that form the strap 11.

FIG. 4 shows the bone end 22 of the ligament graft 21 connected to a single suture 20 that has been passed through hole 23 and through the eyelet slot 19. The bone end 21 is shown as having been pulled fully into the first tunnel section 26 and the strap 11 is shown as having been pulled through footing 15. When pressure on the strap 11 to pull it through the footing 15 is released, or a force is applied to pull the strap back through the footing, a cone skirt edge 13a will slide over the edge of the disk hole 17, prohibiting withdrawal, and allowing the strap to be cut off across the body 12, providing a flat apex cone shaped locking member 13. In practice, the locking member 13 will pass through the footing disk 16 center hole 17 and, during which passage, the cone skirt edge 13a will be somewhat compressed. After which travel of the footing member 13 through the center hole 17, the locking member skirt edge 13a will flex or spring outwardly to its original attitude, so as to extend across the edge of the disk center hole 17, as shown in FIG. 4. So arranged, the skirt edge 13a rests on the edge or lip of footing hole 17 prohibiting the strap 11 from being pulled back through the disk 16. Cutting of the body 12, above the lock member 13, completes the ligament graft end endosteal mounting.

Figure 2:
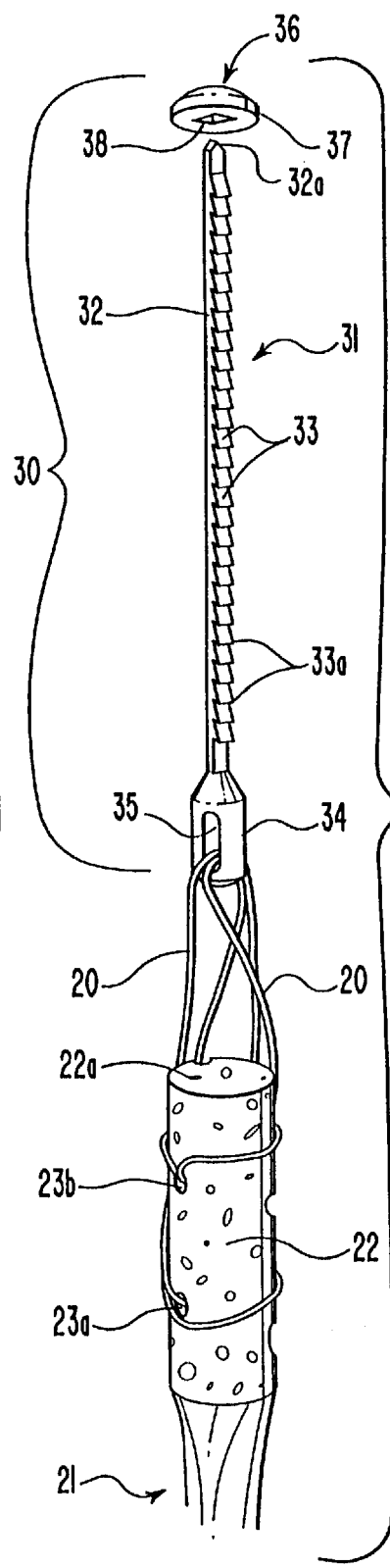
FIG. 2 is a profile perspective view like that of FIG. 1 of a second embodiment of an adjustable length strap and disk shaped footing of the invention showing the strap as including a rack of right angle teeth formed along one edge as the locking members.
Figure 5:
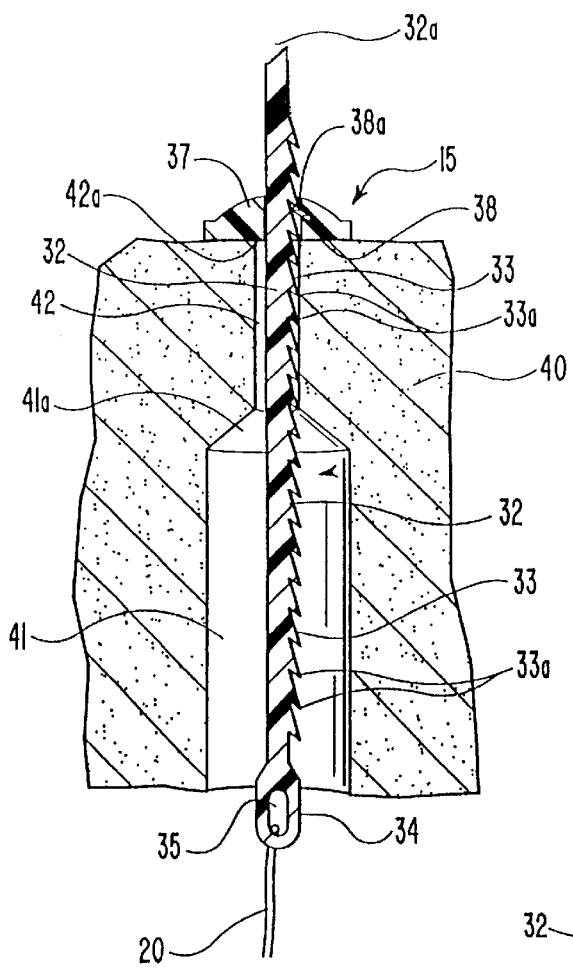
FIG. 5 is a view like FIG. 3 only showing the second embodiment the adjustable length strap and footing for ligament mounting of FIG. 2 with the strap proximal end shown fitted through the footing.

A second embodiment of an adjustable length strap and footing for use as a ligament mounting 30 is shown in FIG. 2, and is hereinafter referred to as ligament mounting 30, with its use shown in FIGS. 5 and 6. The ligament mounting 30, like ligament mounting 10 is preferably for use in endosteally mounting a ligament graft end, shown herein as a bone end 22 of ligament graft 21, in an end 41a of a prepared first straight ligament tunnel section 41 that has been formed in a bone 40. The bone 40, first tunnel section 41 and a second straight tunnel section 42 are like the tunnel sections 26 and 27, described above. The second tunnel section 42, like the second tunnel section 27, extends axially from the first tunnel section, from end 41a thereof and exits the bone cortex at 42a. The function of which first and second tunnel sections 41 and 42 are essentially the same as the tunnel sections 26 and 27 shown and described in relation to FIGS. 3 and 4, and so will not be further described herein.

The ligament mount 30, as shown best in FIG. 2, includes a strap 31 that is shown as having a straight body 32 of a uniform cross section along its length, with three sides that connect at right angles and with a straight rack of equal spaced right angle teeth 33 formed along its fourth side. Each tooth 33 has an apex end 33a with its hypotenuse side sloping towards the strap distal end. The teeth 33 are to each function as a locking member, as set out hereinbelow. A straight body 32 top or proximal end 32a is preferably pointed, and the straight body bottom or distal end is preferably formed into a cylinder 34 wherein a longitudinal slot is formed as an eyelet slot 35, though, of course, a tab with a hole formed therethrough can be so employed to mount a suture sling, or the like thereto within the scope of this disclosure.

A suture or sutures 20 that are arranged as a sling, are shown in FIGS. 2, 7 and 11, and is fitted through the eyelet slot 35 and connect through transverse holes 23a and 23b formed in bone end 22 of ligament graft 21, as described above. With a single suture 20 shown fitted through eyelet slot 35 and connect through bone end 22 transverse hole 23 shown in FIGS. 3, 4, 5 and 6, 8A, 8B, 9 and 10A. These various suture couplings to the ligament end have been set out and described above with reference to the ligament member 21, and ligament member shown in FIGS. 9 and 10A below, and so will not be further described herein. Accordingly, it should be understood that the ligament graft bone end 22 of ligament graft 21 is preferred connected by a suture or sutures to the ligament mountings 10 and 30 and the ligament mountings 45, 55 and 70, within the scope of this disclosure. Also, for example, it should be understood that, a tendon as a ligament graft, could be passed through the eyelet slot 19 or 35 and folding upon itself, forming a two strand ligament graft, within the scope of this disclosure.

A ligament mounting 30 strap 31 body 32 pointed top or distal end 32a, as shown in FIG. 2, are aligned for fitting through a center hole 38 that has been formed through a disk 37, that is a footing 36. In FIG. 5, the strap 31 body 32 pointed proximal end 32a is shown as having passed through the disk 37 hole 38 with the hypotenuse sides of several of the individual teeth 33 shown as having traveled across an edge or lip 38a of the disk 37 hole 38. In which passage the apex end 33a of each tooth 33, in turn, is slightly collapsed inwardly so as to allow it to pass through the hole 38, and will thereafter flexes outwardly to its original attitude after exiting the hole 38, engaging the hole 38 edge 38a.

Figure 6:
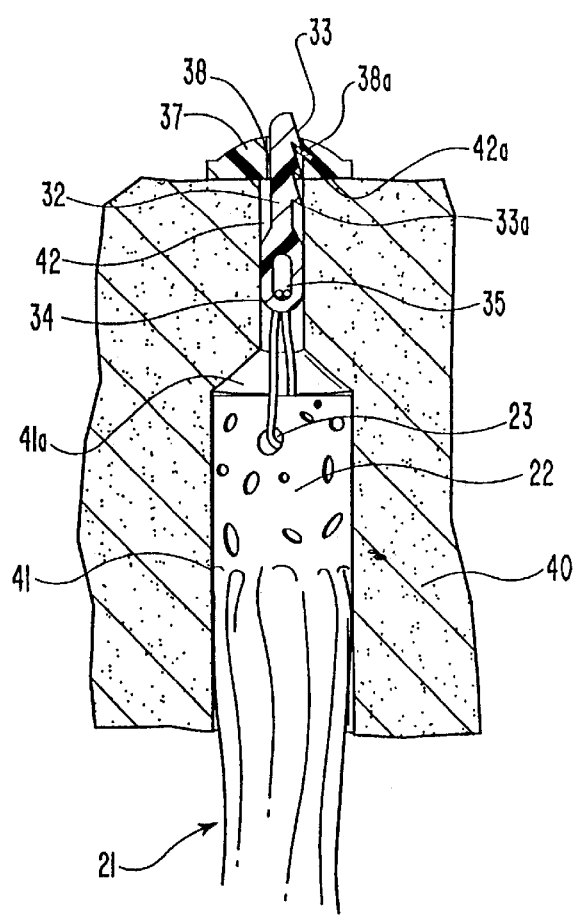
FIG. 6 is a view like that of FIG. 5 only showing the strap as having been pulled through the footing and cut off above a right angle tooth with a bone end of the ligament graft, shown connected to the strap end by a pair of sutures, and positioned in the first tunnel section.

FIG. 6 shows the ligament mounting 30 strap 31 as having been pulled through the footing 36 to where the ligament graft 21 bone end 22 has been pulled into the first tunnel section 41, approximately to the end 41a thereof. Here, it should be understood a, tensile force can be applied through the ligament graft and body 32 to set a tooth 33 apex edge 33a firmly across edge or lip 38a of disk 37 hole 38. The tooth apex surface thereby passes over the disk hole edge to prohibit a pulling of the strap 31 back through the footing 36. So arranged, a permanent ligament graft end endosteal mounting in the first tunnel section 41 is provided. Thereafter, the body 32 can be cut off above the tooth 33 whose apex end 33a engages the disk hole edge or lip 38a, as shown in FIG. 6, completing the ligament mounting.

A third embodiment of an adjustable ligament strap and footing 45 for use for mounting a ligament 21 in a bone tunnel section 50 is shown in FIGS. 7, 8A and 8B. For this embodiment, a sling formed from sutures 20, like the arrangements set out above, is preferably utilized for securing the bone end 22 of ligament graft 21. This sling is also for fitting through transverse holes 23a and 23b, as described above, and accordingly its mounting onto the bone end 22 that includes a flat top 22a, will not be further described herein.

Unique to the suture sling of FIG. 7 is that the pair of sutures 20 have been twisted, braided, or otherwise formed into a chain or cable 46 whose upper or proximal end 47 is aligned for fitting through a footing 48 that is preferably formed as a cylinder as from a soft metal to allow it to be crimped, as with a crimping tool, whose opposing jaws 52a and 52b are shown in FIG. 8A. The jaws 52a and 52b, as shown, are aligned for clamping onto a cylindrical body 51 of the footing 48, crushing the footing center hole 49 tightly onto the cable 46, securing it thereto. The jaws 52a and 52b, as shown in FIG. 8A include opposing surfaces 53a and 53b that are arranged to fit into like surfaces formed over footing body 51. So arranged, a tight non-slip grip is provided to crimp the footing when the opposing tool jaws surfaces 53a and 53b are brought together as shown in FIG. 8B.

In FIG. 8A, the cable 46 is shown fitted through first straight tunnel section 50 and then through a second straight tunnel section 50a, that extends axially from the end of the first tunnel section and exits a bone cortex. Shown in FIGS. 8A and 8B, the cable 46 receives the footing 48 crimped thereon with the footing bottom 51a having a greater diameter than that of the cortex end of the second tunnel section to extend thereacross, precluding the cable 46 that is mounted to the bone end 22 from pulling out of the footing 48, even when the ligament graft 21 is under tension. This completes the ligament mounting. Of course, it should be understood, the cable 46 can be formed of two or more sutures, as shown in FIG. 7, or can be a single suture fitted through a single transverse hole 23, formed through the bone end 22, as shown in FIGS. 8A and 8B or other appropriate chain, cable, or strand within the scope of this disclosure.

Figure 9:
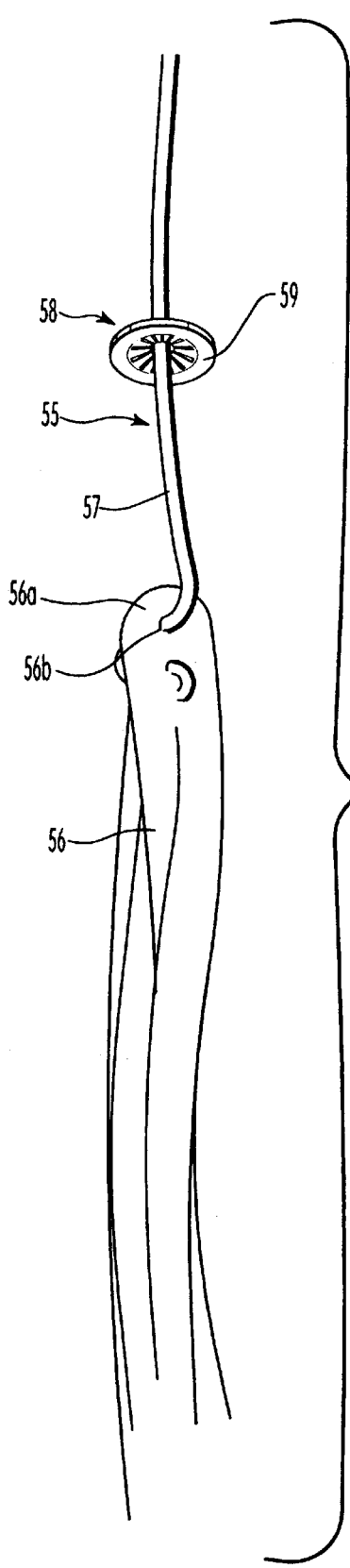
FIG. 9 is a profile perspective view like that of FIGS. 1, 2 and 7, showing a fourth embodiment of an adjustable length strap and footing where the strap is a single strand of a cable, chain, suture, or the like, that has been sewn into a ligament end with the opposite end shown passed through a disk shaped footing that includes radial pie shaped sections around the transverse hole that act as cantilever elements.
Figure 10A:
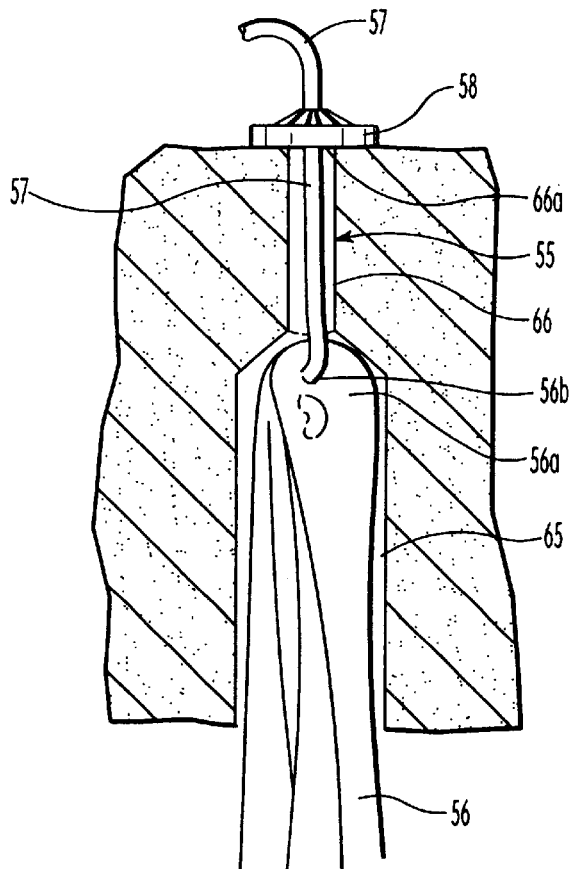
FIG. 10A is a side elevation view like that of FIG. 8 showing first and second tunnel sections with the single strand shown pulled through the second tunnel section and fitted through the footing, with the ligament end shown pulled fully into the first tunnel section, and the single strap shown pulled through the footing urging the ends of the pie shaped segments thereof upwardly that engage the side of the single strand.
Figure 10B:
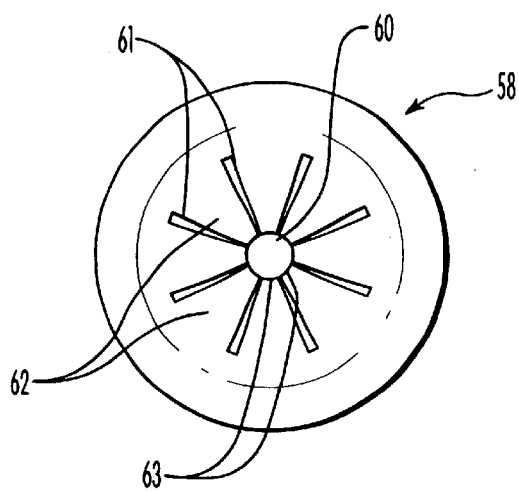
FIG. 10B is a top plan view of the footing of FIGS. 10 and 10A.

Still another or fourth embodiment of an adjustable ligament strap and footing 55 is shown in FIGS. 9 and 10A and is arranged for connection, as by sewing a single cable type strap 57 thereof onto an end 56a of a ligament graft 56, with a footing 58 of which adjustable length strap and footing 55 shown also in FIG. 10B. Shown in FIGS. 9 and 10A, the adjustable length strap and footing 55 preferably includes the cable type strap 57, but can be a suture, metal cable, wire, or the like, within the scope of this disclosure. The strap 57 is connected to end 56a of ligament graft 56 as by passing it through a hole 56b that has been formed therethrough. Thereafter, the strap 57 distal end can be knotted, or the like, to prohibit its being pulled out of the ligament graft end 56a. As shown, the strap 57 can to sewn in the ligament graft end 56a, increasing purchase and pull-out strength, as required.

Like the above described tunnel mountings of the first three embodiments, this fourth embodiment preferably provides for mounting of the ligament graft 56 proximal end 56a in a first straight tunnel section 65, as shown in FIG. 10A, with the strap 57 fitted through a second smaller straight tunnel section 66, that is formed to extend axially from that first tunnel section endosteal end, and exits the bone cortex at 66a, as shown in FIG. 10A. Upon exiting the second tunnel section 66 the footing 58 receives the strap 57 fitted through a center hole 60, as shown in FIG. 10B, and is slid along the strap 57 to the attitude shown in FIG. 10A. The footing 58, to provide for locking to the strap 57, is shown as having a flat disk shaped body 59 with the center hole 60 formed therethrough, as shown best in FIG. 10B. From the center hole 60 a plurality of equal spaced radial slots or grooves 61 are formed into the disk center portion, thereby dividing that disk center portion into like pie shaped sections 62 that each include an apex end 63. In practice, the strap 57 is formed to be slightly larger in diameter than the center hole 60, whereby urging the strap through the hole 60 tends to flex the pie shaped sections 62 upwardly, the pie shaped sections 62 each functioning as cantilever elements, as shown in FIGS. 9 and 10A. With the footing engaging the bone cortex, spanning the second tunnel section cortex end 66a, the pie shaped section 62 apex 63 tend to engage the strap 57 side when a force is applied on the ligament graft 56 to pull it and the connected strap 57 out of the first tunnel section, providing for locking the footing 58 onto the strap 57, completing the ligament graft 56 mounting, as shown in FIG. 10A.

A final or fifth embodiment of the present invention in an adjustable ligament strap and footing 70 is shown in FIG. 11. This fifth embodiment is also for use for mounting a bone end 22 of a bone tendon bone ligament graft 21 in a first straight tunnel section formed in a bone, as described above. In this mounting, a straight bar 71 is fitted through a second straight tunnel section that extends axially from the endosteal end of the first tunnel section, the bar 71 exiting the bone cortex, as set out above. Accordingly, the first and second tunnel sections, as shown in FIGS. 3, 4, 5, 6, 8A, 8B and 10B, it should be understood, are also preferred for use with this fifth embodiment and will not be further described herein. Similarly, this fifth embodiment can be used with a sling arrangement like those described above, for mounting a suture sling formed from sutures 20 fitted through transverse holes 23a and 23b formed in a bone end 22 having a flat top end 22a, and so will not be further described herein. Though, it should be understood, this fifth embodiment can be used with any connecting arrangement for linking it to a ligament graft, within the scope of this disclosure.

Like the above set out first and second embodiments, this fifth embodiment includes a distal section 72 formed with a hole 73 therethrough as an eyelet end for receiving the sutures 20 passed therethrough. Further, as shown in FIG. 11, a top or proximal end 74 of bar 71 is shown squared off, though it can be pointed, aligned to fit through a hole 77, in disk 75, which hole 77 is shown as having a rectangular shape, that is formed through the center of a disk body 76. The disk 75 is shown as being flat and is the footing of this embodiment. The disk body 76, as shown, includes a pair of parallel spaced lateral slots 78a and 78b formed at right angles from the hole 77 into the disk body, to leave a center section 79 therebetween. The center section 79, as shown, has a flat outer edge 80 that extends into the slot 77 and is to function as a locking pawl to flex upwardly as the bar 71 is passed therethrough, with outer edge 80 to flex into binding against the bar surface when a force is applied to pull the ligament graft and connected bar out from the tunnel sections. The center section 79 thereby functions as a locking pawl to slide along a flat surface and to ratchet over an uneven surface, such as a chain, cable, or the like. So arranged, the center section edge 80, as shown, tends to bind into the bar 71 surface prohibiting its withdrawal and to permanently lock the bar 71 footing 75 in place over the second tunnel section cortex end, completing the mounting. With, for a bar 71 with an other than flat surface, the edge 80 will travel thereover and lock in a slot, groove, depression, or the like, completing the mounting.

While preferred embodiments of ligament mountings 10, 30, 40, 55 and 70 and their function for endosteally mounting an end of a ligament graft in a prepared tunnel section have been shown and described herein, it should be understood that the present disclosure is made by way of example only and that variations and changes are possible without departing from the subject matter and reasonable equivalency thereof coming within the scope of the following claims, which claims we regard as our invention.

We claim:

1. An adjustable length strap and footing for mounting a ligament comprising, a strap means that includes a section of material configured to be connected on one end to a ligament graft; a footing that is formed to have essentially a cylindrical shape from a soft metal to have a flat undersurface configured to contact a bone cortex and having a surface area that is greater than a cross section of said strap means and a bone tunnel section wherethrough said strap means is to be fitted and said footing includes a center hole formed therethrough to provide for passage of an opposite end of said strap means; and a crimp locking means of said footing that will allow passage of said strap means through said footing and can be crimped to collapse a portion of said footing into said center hole, gripping a surface of said strap means against movement when a tensile force is applied thereto that attempts to pull said strap means back through said footing.

2. The adjustable length strap and footing for mounting a ligament as recited in claim 1, wherein the section of material is a section of a flexible cord type material; and the footing is formed as a cylinder of a soft metal that will collapse into the center hole when opposing forces are applied to opposite sides of said cylindrical footing, crimping said footing material onto said section of flexible material.

3. The adjustable length strap and footing for mounting a ligament as recited in claim 2, wherein the section of flexible material is a plurality of sutures that have been wound together; and the footing is formed as a cylinder from a soft metal wherein spaced grooves are formed therearound for receiving jaws of a crimping tool.

4. The adjustable length strap and footing for mounting a ligament as recited in claim 3, wherein the section of flexible material is a pair of sections of suture material that have been wound together.

5. A method for endosteally mounting an end of a ligament graft in a prepared bone tunnel section comprising the steps of, forming a tunnel into a section of bone that exits a bone cortex; securing a ligament graft end to a strap and providing a footing having a diameter greater than that of said bone cortex tunnel end and includes a center hole for fitting said strap therethrough, and which said footing is formed of a soft metal material that can be collapsed by crimping it to collapse a center hole section into said strap as a locking member means, which said center hole section allows passage of said strap through said footing and when crimped to bind said strap and footing together prohibits said strap from being pulled from said footing; fitting a proximal end of said strap through said bone tunnel section; aligning said footing center hole with an opening from said bone tunnel section to receive said strap proximal end; with an undersurface of said footing engaging the bone cortex across said bone tunnel section end, drawing said strap through said footing center hole and applying opposing jaws of a crimping tool to said footing and crimping said footing such that said locking member means binds said strap and footing together.

6. A method for endosteally mounting an end of a ligament graft in a prepared bone tunnel section as recited in claim 5, wherein the bone tunnel consists of a first tunnel section formed into the bone; and includes, from an end of said first tunnel section in the bone endosteum, a second tunnel section formed to extend axially therefrom, exiting the bone cortex.

7. The method for endosteally mounting an end of a ligament graft in a prepared bone tunnel section as recited in claim 5, further including the step of, after crimping the footing onto the strap, removing a portion of the strap above the footing that is in engagement with a center hole lip.

8. The method for endosteally mounting an end of a ligament graft in a prepared bone tunnel section as recited in claim 5, wherein the footing is formed from a soft metal as a short cylinder having a flat bottom surface and is grooved at spaced intervals therearound for receiving opposing jaws of a crimping tool fitted thereto to subject walls of said cylinder to a compressive force applied thereacross to collapse said cylinder center hole opposing walls together, crimping said footing onto the strap.

* * * * *